(12) United States Patent
Malo

(10) Patent No.: US 8,142,192 B2
(45) Date of Patent: Mar. 27, 2012

(54) DEVICE FOR TRANSFERRING THE POSITION OF AN ANGLED ABUTMENT FROM A MODEL TO AN IMPLANT

(75) Inventor: Paulo Malo, Lisbon (PT)

(73) Assignee: Nobel Biocare Services AG, Glattbrugg (CH)

( * ) Notice: Subject to any disclaimer, the term of this patent is extended or adjusted under 35 U.S.C. 154(b) by 870 days.

(21) Appl. No.: 12/031,607

(22) Filed: Feb. 14, 2008

(65) Prior Publication Data
US 2009/0047628 A1 Feb. 19, 2009

Related U.S. Application Data

(60) Provisional application No. 60/999,736, filed on Feb. 21, 2007.

(51) Int. Cl.
*A61C 8/00* (2006.01)

(52) U.S. Cl. .................................... 433/173; 433/213

(58) Field of Classification Search ............... 433/75, 433/76, 172–176, 72, 213, 214, 223, 191–196; 700/98
See application file for complete search history.

(56) References Cited

U.S. PATENT DOCUMENTS
2008/0153063 A1* 6/2008 Mullaly et al. .............. 433/174
* cited by examiner

*Primary Examiner* — Sunil K Singh
(74) *Attorney, Agent, or Firm* — Knobbe, Martens, Olson & Bear, LLP.

(57) ABSTRACT

A method is provided for transferring the position of an angled abutment from a model to an implant installed in the jawbone of a patient. The method can include attaching an attachment member to the first implant replica, attaching an angled abutment to the second implant replica, attaching an abutment holder to the angled abutment, connecting a connecting member to the attachment member, connecting the connecting member to the abutment holder, releasing the attachment member from the first implant replica, and releasing the angled abutment from the second implant replica.

20 Claims, 5 Drawing Sheets

DEVICE FOR TRANSFERRING THE POSITION OF AN ANGLED ABUTMENT FROM A MODEL TO AN IMPLANT

PRIORITY INFORMATION

This application is a non-provisional of U.S. Patent Application 60/999,736, which was converted to a provisional application from U.S. patent application Ser. No. 11/677,534, filed Feb. 21, 2007, the entire contents of which are hereby incorporated by reference herein.

BACKGROUND OF THE INVENTION

1. Field of the Invention

The present invention relates to a device for transferring the position of an angled abutment from a model to an implant installed in the jawbone of a patient.

2. Description of the Related Art

A dental restoration, such as a prosthetic bridge, may be attached to an edentulous jaw by means of implants. Four implants may be used to fix a single dental restoration either in the upper or the lower jaw. Using only four implants, two posterior and two anterior implants, in the edentulous jaw can take the benefit of tilting the two posterior implants up to a maximum of approximately 45 degrees relative a longitudinal axis of the anterior implants. The anterior implants, in turn, are normally positioned with their longitudinal axes parallel to a normal of a surface of the jawbone. Tilting the posterior implants has e.g. the advantage that longer implants may be used and that coronal ends of the tilted implants, to which the dental restoration may be attached, will be further apart compared to using substantially parallel installed implants. Furthermore, it may not be possible to position the posterior implants straight due to anatomical structures, such as nerves located in the jawbone. However, with a tilted implant, penetrating the nerve can be avoided and still provide sufficient space between top surfaces of the implants to e.g. provide for a stable support structure for a dental bridge.

An abutment is used between the implant and the dental restoration e.g. to properly seat the dental restoration to the implant. For a tilted posterior implant, an angled abutment can be used whereas a straight or a slightly angled abutment can be used for an anterior implant. The angled abutments for the tilted posterior implants can be angled 30 degrees relative a longitudinal axis of the implant. If an angled abutment is used for the anterior implant, the abutment can be angled 17 degrees relative the longitudinal axis of the anterior implant.

Each of the implant and the abutment can have anti-rotational features, which are also referred to as indexing means. The indexing means may e.g. comprise a multi-sided interface, such as a hexagonal interface. The indexing means provides a fixed rotational relationship between the implant and the abutment. If indexing means is used, the abutment is connected to the implant in a stepwise rotational relationship. Thus, the rotational position of the abutment relative the implant is set by the indexing means. The rotational position can be manually adjusted to provide a desired rotationally relationship or orientation between the implant and the abutment.

Using conventional surgery, such as flap surgery, the four implants are installed in the jawbone of a patient. The implants are tightened using e.g. a torque wrench to a predetermined value, such as 35-45 Ncm. Then, an abutment is attached to each implant. After suturing, an impression coping may be attached to the abutment. An impression using e.g. silicon soft putty material may be taken for transferring the position of the abutment to a stone model. The impression includes the rotational position relative the jawbone, and thus relative the installed implants, of the angled abutments installed on the posterior implants. Then, the dental restoration can be fabricated based on the stone model with installed implant replicas and abutments. To provide a proper fit between connection members of the dental restoration and the abutments, the rotational position of the angled abutments relative the jawbone/model is used when the dental restoration is fabricated. For straight abutments, the rotational position is not an issue.

A surgical template may be used to install implants substantially vertical or slightly tilted relative the surgical template. The position of the implants can be preplanned using a CAD (Computer Aided Design) procedure, such as the Procera® system provided by Nobel Biocare®. The surgical template as well as the dental restoration may be prefabricated based on data from the CAD procedure prior to installing the implants in the jawbone. When a surgical template is used during surgery, the implant is installed to a predetermined depth. When the implants are installed substantially vertical or slightly tilted relative the surgical template, straight abutments may be used. Hence, the rotational position of the straight abutment relative the implant is not an issue.

It has been proposed to use a surgical template also for installing implants tilted up to approximately 45 degrees. Hence, angled abutments will be required. It has also been proposed to manufacture a dental restoration, which requires angled abutments, prior to installing the implants. Thus, the surgical template and the dental restoration can be provided at the same time and the dental restoration installed as soon as the implants have been installed. However, a prefabricated dental restoration presumes a predetermined rotational position of the angled abutments relative the jawbone and thus the tilted implants. When a surgical template is used, the dental restoration has not been based on the position of the implants as installed in the jawbone of the patient, as in the case of conventional surgery. Hence, any angled abutment has to be positioned relative the implant to fit the rotational position presumed when the dental restoration was manufactured. This can be cumbersome. For angled abutments, there may be a conflict between the depth of the implant in the jawbone and the rotational position of the angled abutment on the implant. It is difficult, if not impossible, to control the rotational position of the angled abutment relative the jaw bone/installed implant such that it fits the prefabricated dental restoration. It may be difficult e.g. if the abutment has to be tightened to the implant before the dental restoration is tightened to the angled abutment. If the implant and the abutment have indexing means, correct rotational positioning of the angled abutment becomes even more cumbersome, as the depth of the implant in the jaw bone and the rotational position of the indexing means of the implant would have to be controlled at the same time. In some situations, it may even be impossible to provide a proper fit between the angled abutment and the dental restoration. For example, the indexing means of the angled abutment and the indexing means of the tilted implant may not mate at the rotational position desired.

SUMMARY OF THE INVENTION

According to some embodiments of the invention, a device for transferring the position of an angled abutment from a model to an implant installed in the jawbone of a patient, comprises: an attachment member operative to temporarily attach the device to a first implant installed in the jaw bone of a patient; an abutment holder operative to temporarily hold the angled abutment; and a connecting member fixable to the attachment member and the abutment holder and being operative to connect the abutment holder to the attachment member in a fixed spatial relationship, whereby the angled abutment is alignable to a predetermined position relative a second implant installed in the jaw bone of the patient when the attachment member is temporarily attached to the first implant, the abutment holder holds the angled abutment, and the connecting member is fixed to the attachment member and the abutment holder.

According to some embodiments of the invention, a kit of components for assembling a device for transferring the position of an angled abutment from a model to an implant installed in the jawbone of a patient, comprises: an attachment member operative to temporarily attach the device to a first implant installed in the jaw bone of a patient; an abutment holder operative to temporarily hold the angled abutment; and a connecting member operative to be fixed to the attachment member and the abutment holder and being operative to connect the abutment holder to the attachment member in a fixed spatial relationship.

According to some embodiments of the invention, a method for assembling a device for transferring the position of an angled abutment from a model to an implant installed in the jawbone of a patient, said method comprises: installing a first implant replica in a model; installing a second implant replica in the model; attaching an attachment member to the first implant replica; attaching an angled abutment to the second implant replica; attaching an abutment holder to the angled abutment; connecting an connecting member to the attachment member; connecting the connecting member to the abutment holder; releasing the attachment member from the first implant replica; and releasing the angled abutment from the second implant replica.

Further embodiments of the invention are defined in the dependent claims.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

Further objects, features and advantages of embodiments of the invention will appear from the following detailed description, reference being made to the accompanying drawings, in which.

DETAILED DESCRIPTION OF THE PREFERRED EMBODIMENTS

Figure 1:
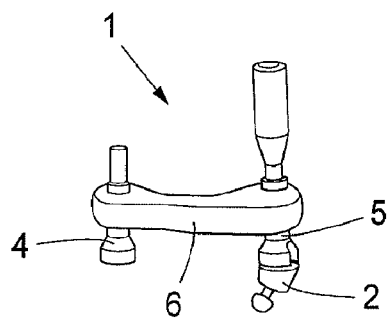
FIG. 1 is a perspective view of an embodiment of the device for transferring the position.

FIG. 1 illustrates a device 1 for transferring the position of an angled abutment 2 from a model 3 (FIG. 2) to an implant installed into the jawbone of a patient (not shown). The device 1 comprises an attachment member 4, an abutment holder 5, and a connecting member 6. The device 1 can be used for transferring the ultimate position of the angled abutment 2 from the model 3 to the patient. The device 1 can be used for guided surgery, where a surgical template 7 (FIG. 7) is used for properly positioning of implants in the jawbone of the patient. Using embodiments of the present invention, the device 3 can be used for positioning the angled abutment 2 on a tilted implant installed into the jawbone of the patient. The tilted implant may e.g. be tilted up to approximately 45 degrees relative a normal to the jawbone at the position at which the implant penetrates or enters the jawbone. The surgical template 7, a dental restoration 8 (FIG. 8), and the device 1 can be prefabricated before the implants are installed into the jawbone of the patient.

Figure 2:
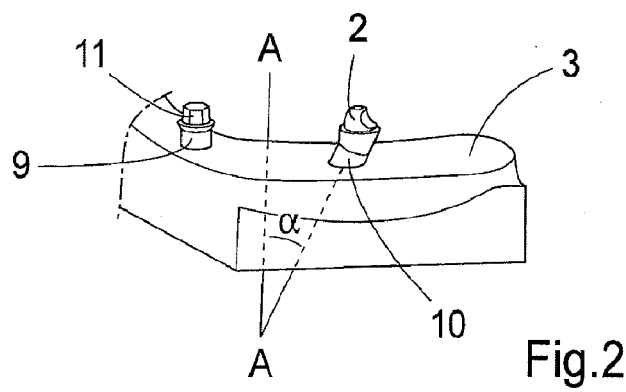
FIG. 2 is a perspective view of a portion of a model of a jawbone.

FIG. 2 illustrates a portion of the model 3, in which a first implant replica 9 and a second implant replica 10 has been installed. For the manufacturing of the model 3 and installation of the first and second implant replicas 9, 10 and the angled abutment 2, see below. The second implant replica 10 is tilted a degrees relative a normal of the surface of the model 3. In FIG. 2, the normal is indicated by the axis A-A. The position of the normal for the determination of the angle α is approximately at the position of the surface of the model at which the implant second implant replica 10 penetrates or enters the surface. α may e.g. be in the range of approximately 15-45 degrees. The angle α is also applicable for the tilted implant discussed above. An implant or implant replica positioned straight are positioned substantially parallel to said normal.

A straight abutment 11 is attached to the first implant replica 9. The angled abutment 2 is attached to the second implant replica 10. For illustrative purposes, only two implant replicas are shown in FIG. 2. Only two implant replicas are required for assembling the device 1 according to this embodiment of the invention. However, additional implant replicas, positioned tilted or straight, can be provided in the model 3. The angled abutment 2 has been positioned on the second implant replica 10, as will be described below. The position of the angled abutment 2 relative the second implant replica 10 is the same when the device 1 is assembled as when the dental restoration 8 is prepared for proper seating with the second implant replica 10. The device 1 will be used to transfer the position of the angled abutment 2 from the model 3 to an implant installed in the patient. Hence, the position of the angled abutment 2 relative the second implant replica 10 will be the same as the position relative an implant installed in the jawbone of the patient.

The angled abutment 2 has a certain rotational position relative the second implant replica 10. The straight abutment 11 and the angled abutment 2 are temporarily fixed to the first implant replica 9 and the second implant replica 10, respectively, by fastening members (not shown in FIG. 2). The rotational position of the straight abutment 11 is not an issue, as discussed in the background of the invention section. However, the rotational position of the angled abutment 2 relative the second implant replica should be transferred to an implant installed in the jaw bone of the patient. For this purpose, the device 1 according to embodiments of the invention can be used.

Figure 3A:
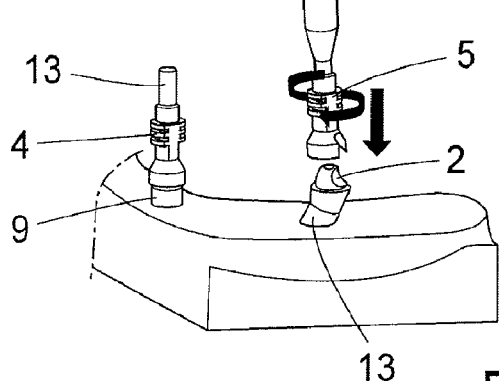
FIGS. 3A-3C are perspective views of the portion of the model of the jawbone with an embodiment of the device for transferring the position in partly assembled states.
Figure 3B:
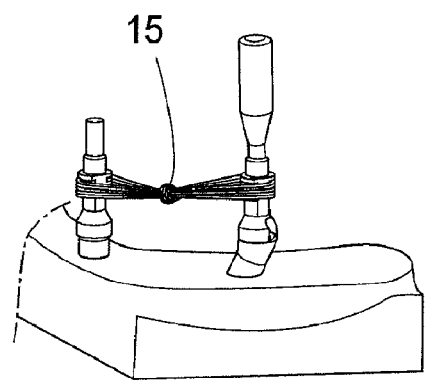
Figure 3C:
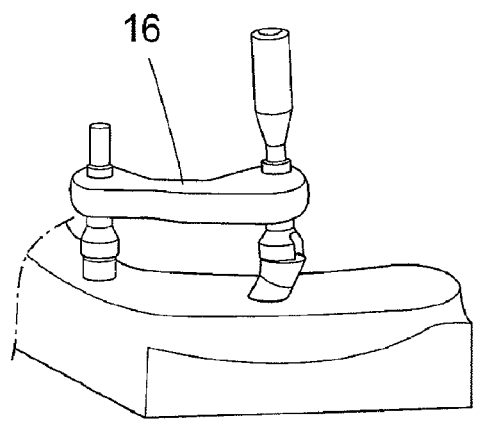

FIGS. 3A-3C illustrate an embodiment of a method for assembling the device 1. The attachment member 4 is temporarily attached to the first implant replica 9. The abutment holder 5 is temporarily attached to the angled abutment 2. The angled abutment 2 is attached to the second implant replica 10. The attachment member 4 is tightened to the first implant replica 9 with a fastening member 13 of the attachment member 4. The abutment holder 5 is tightened to the angled abutment 2 by a fastening member 14 of the abutment holder 5. Hence, a fixed spatial relationship between the attachment member 4 and the abutment holder 5 is provided. Then, the connecting member 6 is connected to the attachment member 4 and to the abutment holder 5. A fixed spatial relationship is provided between the attachment member 4 and the connecting member 6. Also, a fixed spatial relationship is provided between the abutment holder 5 and the connecting member 6. Hence, a fixed spatial relationship is also provided between the attachment member 4 and the abutment holder 5. The fixed spatial relationship between the attachment member 4 and the abutment holder 5 is maintained by the connecting member 6 when the attachment member 4 is released from the first implant replica 9 and the angled abutment 2 is released from the second implant replica 10.

In the embodiment of FIGS. 3B-3C, the connecting member 6 comprises a wire 15 and acrylic resin 16. The acrylic resin 16 can be applied around the wire 15. When the acrylic resin 16 has settled, the fixed spatial relationship between the attachment member 4 and the abutment holder 5 is provided.

The acrylic resin may be a relatively quick settling acrylic resin, such as the resin provided under tradename DuraLay sold by Reliance Dental Manufacturing Co., Worth, Ill., USA.

In some embodiments, the wire 15 is dental floss.

In some embodiments, the connecting member 6 comprises at least one elongated rod having a fastening member at each of its ends. The fastening member may e.g. be a releasable clamp. In another embodiment, the fastening member is a releasable coupler. The fastening member is operative to fix the connecting member 6 to the attachment member 4 and the abutment holder 5.

Figure 4A:
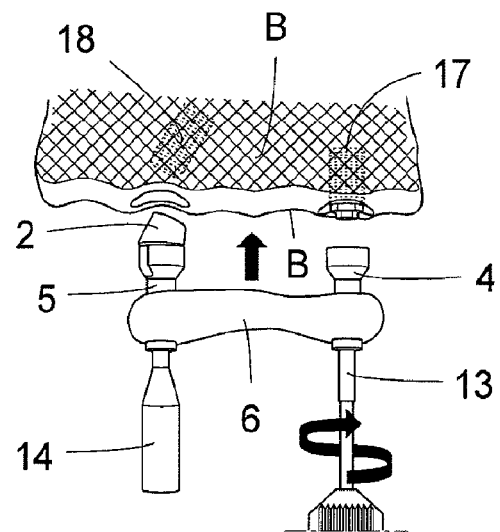
FIGS. 4A-4B are perspective views of an embodiment of the device for transferring in an assembled state.
Figure 4B:
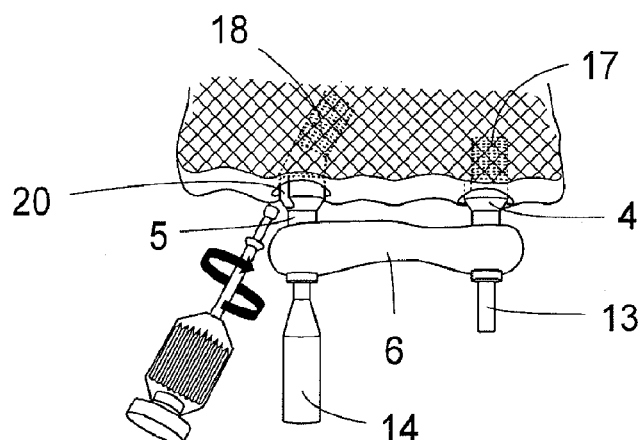

FIGS. 4A-4B illustrate alignment of the angled abutment 2 with an implant installed in the jawbone of a patient. The straight abutment 11 is fixed to a first implant 17. The straight abutment 11 of FIGS. 4A-4B need not be the same as the straight abutment used on the model 3. A second implant 18 is tilted relative the first implant 17 and/or relative said normal. The first and the second implants 17 18 have been installed using the same or a corresponding surgical template 7 that was used to position the first and second implant replicas 9, 10 in the model 3. The spatial relationship between the first and the second implants 17, 18 corresponds to the spatial relationship between the first and the second implant replicas 9, 10. To align the angled abutment 2, which is held by the abutment holder 5, with the second implant 18 the attachment member 4 is temporarily attached to the first implant 17 via the straight abutment 11. In an alternative embodiment, the attachment member 4 is attached directly to the first implant 17. The fastening member 13 of the attachment member 4 may be used to secure the attachment member 4 to the first implant 17. When the attachment member 4 is attached to the first implant 17 and the angled abutment 2 is held over the second implant 18, the angled abutment 2 can be properly aligned with the second implant 18. The angled abutment 2 and the second implant 18 are properly aligned e.g. when a connection interface of the angled abutment 2 and a connection interface of the second implant 2 are aligned. The connection interface of the angled abutment comprises e.g. a bore and the connection interface of the second implant 2 comprises e.g. a threaded bore. When the bores of the connection interfaces are aligned, the angled abutment 2 and the second implant 18 are properly aligned.

In other embodiments, the bridge is mounted directly on the implant positioned straight, whereby a straight abutment is omitted.

The angled abutment 2 can be attached to the second implant using a fastening member 19. The fastening member may e.g. be a fastener, such as a threaded screw or bolt. When the angled abutment 2 has been secured to the second implant 18, the attachment member 4 can be released from the first implant 17 and the abutment holder 5 can be released from the angled abutment 2.

In some embodiments, the fastening member 19 is accessible through an access window 20 of the abutment holder 5.

Figure 5:
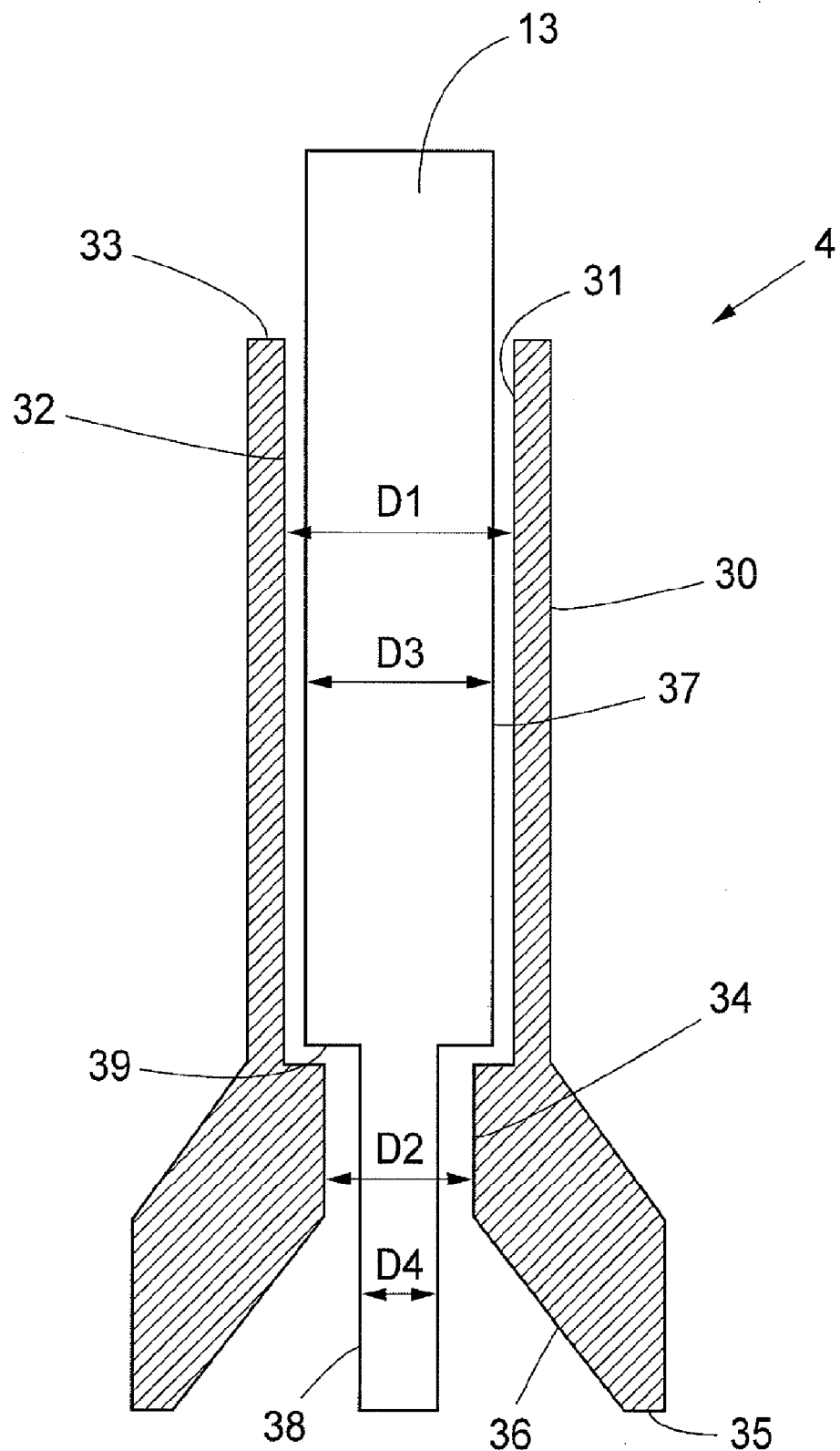
FIG. 5 is a cross-sectional view of an embodiment of the attachment member.

FIG. 5 illustrates an embodiment of the attachment member 4. In the embodiment of FIG. 5, the attachment member 4 comprises a sleeve 30 having a through bore 31. A first region 32 of the through bore 31 at a first end 33 of the sleeve 30 has a first diameter D1. A second region 34 of the through bore 31 proximate a second end 35 of the sleeve 30 has a second diameter D2. The first diameter D1 is larger than the second diameter D2. From the second region 34 towards the second end 35, the through bore 31 widens to form a truncated cone 36. Fastening member 13 has a first diameter D3 at a first portion 37 and a second diameter D4 at a second portion 38. The second portion 38 is threaded. Diameter D3 is smaller than diameter D1 and larger than diameter D2. Diameter D4 is smaller than diameter D2. Thus, the second portion 38 of fastening member 13 extends through the second region 34 in the assembled state of the attachment member 4 and can be attached to a threaded bore (not shown) of the straight abutment 11. An end 39 of the first portion 37 is seated at an end of the second region 34 of the sleeve 30.

In some embodiments, the inner surface of the truncated cone 36 is conical. Thus, the attachment member 4 does not have any indexing means or index features and is thus non-indexing. In other embodiments, the attachment member 4 has indexing means (index features). The indexing means may be provided at the area of the truncated cone.

In some embodiments, the attachment member 4 is a temporary coping and the fastening member 13 is a guide pin.

Figure 6:
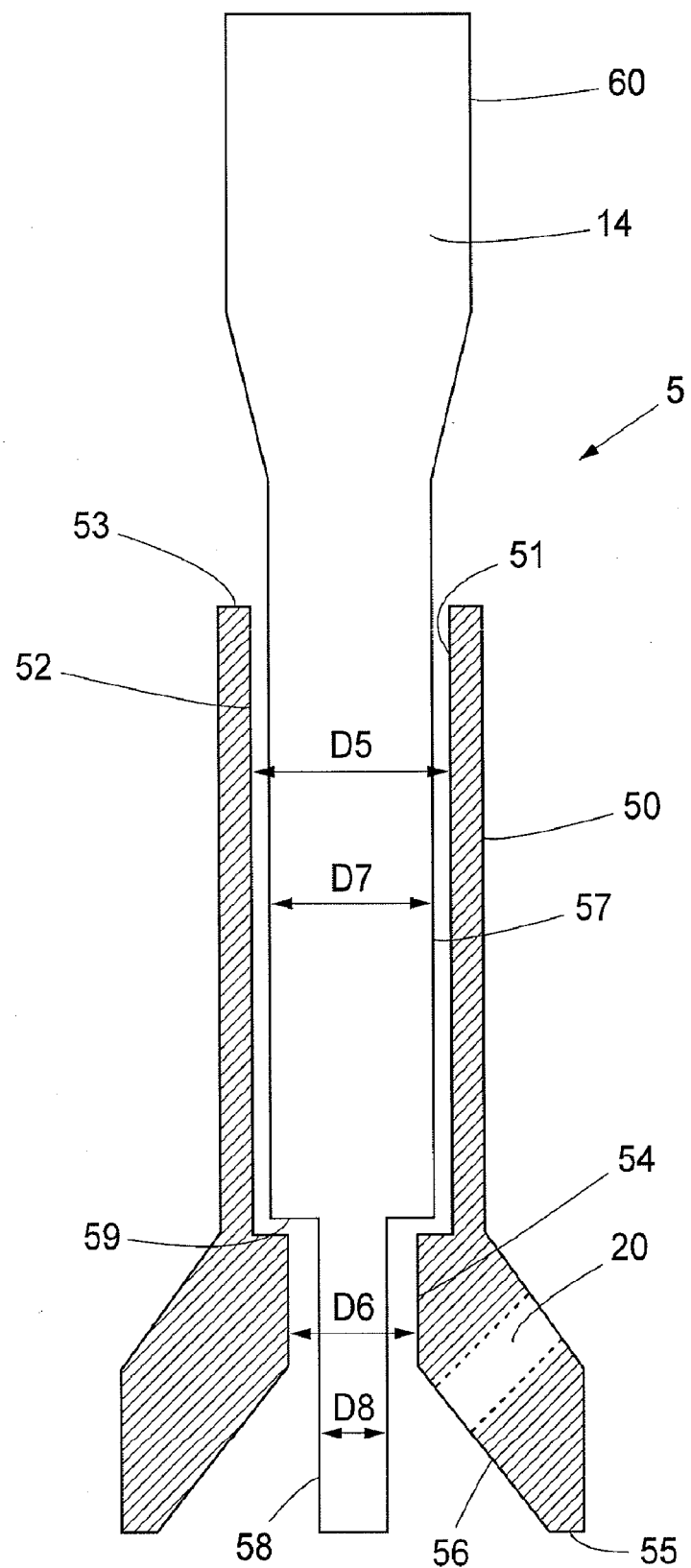
FIG. 6 is a cross sectional view of an embodiment of the abutment holder.

FIG. 6 illustrates an embodiment of the abutment holder 5. In the embodiment of FIG. 6, the abutment holder 5 comprises a sleeve 50 having a through bore 51. A first region 52 of the through bore 51 at a first end 53 of the sleeve 50 has a first diameter D5. A second region 54 of the through bore 51 proximate a second end 55 of the sleeve 50 has a second diameter D6. The first diameter D5 is larger than the second diameter D6. From the second region 54 towards the second end 55, the through bore 51 widens to form a truncated cone 56. Fastening member 14 has a first diameter D7 at a first portion 57 and a second diameter D8 at a second portion 58. The second portion 58 is threaded. Diameter D7 is smaller than diameter D5 and larger than diameter D6. Diameter D8 is smaller than diameter D6. Thus, the second portion 58 of fastening member 14 extends through the second region 54 in the assembled state of the abutment holder 5 and can be attached to a threaded bore of the angled abutment 2. An end 59 of the first portion 57 is seated against an end of the second region 54 of the sleeve 50. The second portion 57 of fastening member 14 extends through the second region 54 to hold the angled abutment 2.

In the embodiment of FIG. 6, the access window 20 is positioned at the region of the sleeve 50 formed as a truncated cone 56. Furthermore, fastening member 14 comprises a handle 60 at an end of its first portion 57. Thus, fastening member 14 can be rotated without using a tool. Hence, fastening member 14 is more convenient to operate when the device is attached to the second implant 18. The second implant 18 may e.g. be located such that it is difficult to access fastening member 14 using a tool.

In some embodiments, the inner surface of the truncated cone 36 is conical. Thus, the abutment holder 5 does not have any indexing means and may provide a non-engaging interface for the abutment to which it should be attached. In other embodiments, the abutment holder 5 has indexing means.

In some embodiments, the abutment holder 5 is a temporary coping modified by providing the access window 20. The fastening member 14 is in some embodiments a guide pin modified by providing the handle 60.

In some embodiments, sleeve 30 and/or sleeve 50 is/are cylindrical.

Figure 7:
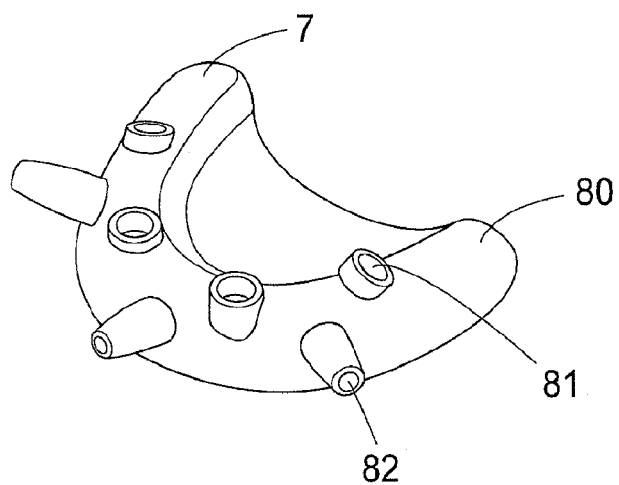
FIG. 7 is a perspective view of a surgical template.

FIG. 7 illustrates an embodiment of the surgical template 7. The surgical template may be fabricated as is generally known in the art. Reference herefore is e.g. made to WO/2003/055407 by the same applicant as the present invention and which is incorporated herein in its entirety by reference. According to an embodiment, the surgical template 7 is prepared using a CAD procedure, such as the Procera® system provided by Nobel Biocare®. Furthermore, the surgical template 7 may contain all information necessary for making the model 3. The dental restoration 8 may in turn be fabricated based on and/or adapted to the model 3.

The surgical template comprises a supporting frame 80 and at least one sleeve 81. A cylinder (not shown) mates with the sleeve 81 and is used during the production of the model 3. A pin (not shown) may be used to secure the cylinder to the sleeve 81. The surgical template may also comprise at least one anchor pin sleeve 82 and a corresponding number of anchor pins (not shown).

Figure 8:
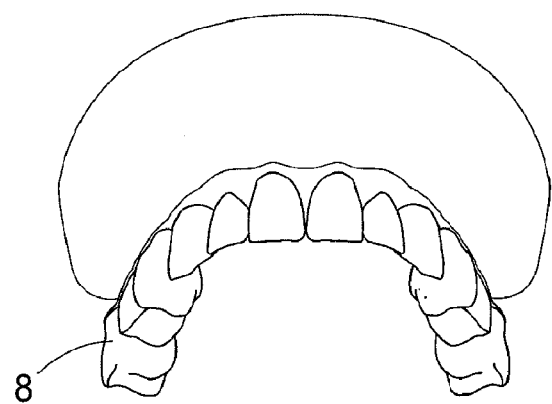
FIG. 8 is a perspective view of a dental restoration.

FIG. 8 illustrates a dental restoration 8. The dental restoration 8 may be a temporarily or permanent dental restoration. In some embodiments, the dental restoration comprises a prosthesis. The prosthesis may comprise a dental bridge.

Figure 9:
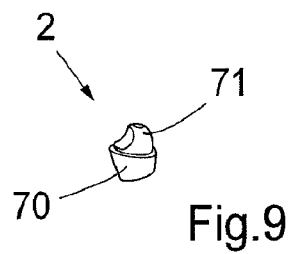
FIG. 9 is a side view of an angled abutment.

FIG. 9 illustrates an embodiment of the angled abutment 2. In the embodiment of FIG. 9, the angled abutment 2 is non-indexing. An abutment is angled when first and second interfacing surfaces 70, 71 are angled in relation to each other. The first and the second surfaces are arranged to mate with an implant and a component for securing the dental restoration to the angled abutment, respectively. In the embodiment of FIG. 9, a normal of the first interface surface 70 is angled 30 degrees relative a normal of the second interface surface 71. In other embodiments, said normals are angled in the range of 15-45 degrees relative each other.

According to some embodiments of the invention, the model 3, the dental restoration 8, the surgical template 7, and the device 1 are prefabricated before the implants 17, 18 are installed into the jawbone of the patient.

To produce the model 3, the implant replicas 9, 10 are installed in the surgical template 7. Each of the implant replicas 9, 10 are secured to the sleeves 81 by means of pins. The cylinder is installed between the sleeve 81 and the implant replica 9, 10. The anchor pin(s) is/are inserted into the anchor pin sleeve(s) 82. A lubricant, such as Vaseline, may be used to lubricate the bottom of the cylinder with the pin and the inner top surface of the surgical template 7. Hence, soft tissue replica added to the surgical template will be easier to dismount.

Soft-tissue replica is provided at the inner top surface of the surgical template 7 and around the implant replicas 9, 10 where they meet the surface of the surgical guide 7. Soft-tissue replica or boxing wax may be used on the buccal side of the vestibular extension of the surgical template 7 to prevent the surgical template 7 from locking when the plaster has set. Then plaster may be poured into the surgical template 7. After the plaster has set, the anchor pin(s) is/are removed. Then, the pin and the cylinder and the surgical template are removed from the set plaster. Hence, the model 3 with the implant replicas properly installed therein is provided.

The plaster may comprise die stone model plaster.

To produce the device 1, the angled abutment 2 is attached to the second implant replica 10. If the device 1 requires that a straight abutment 11 is used, the straight abutment 11 is attached to the first implant replica 9. The abutments 2, 11 may be tightened using a tightening tool, such as screwdriver. When the angled abutment 2 has been mounted, it may be assembled with the abutment holder 14. The abutment holder 14 is then aligned with the longitudinal axis of the straight abutment 11 or the first implant 9. Then, the fastening member for the angled abutment 2 is tightened. Thus, the angled abutment 2 has been properly aligned with the second implant replica 10.

To fabricate or prepare the dental restoration, copings may be placed on the abutments 2, 11 attached to the implant replicas 9, 10. The copings may be secured using guide pins and fasteners, such as screws. The copings may be temporary copings.

The dental restoration may e.g. be fabricated using an all-acrylic bridge, which comprises a high-density acrylic.

If the dental restoration 8 is a full bridge to be placed on four implants, temporary copings may be placed on the two anterior implant replicas and one on one of the posterior implant replicas before the dental restoration is fabricated. When the dental restoration has been fabricated, a bore may be drilled through the dental restoration 8 at the position where the fourth coping should be positioned. The bore may be larger than the coping to provide for adjustment possibilities. Then, the dental restoration is attached to the implant replicas using the copings installed in the dental restoration and the final coping is tried in at the bore but not secured to the dental restoration 8.

When the dental restoration should be installed to the implants 17, 18 installed in the jawbone of the patient, the copings pre-installed in the dental restoration are first fixed to the implants. Then, a coping is inserted into the bore of the dental restoration and tightened to an implant accessible through said bore. Finally, a composite or acrylic may be filled between the bore and the coping to secure the coping to the dental restoration. If necessary, the coping may be reinforced and adjusted when the dental restoration 8 is disconnected from the implant.

The device 1 can be delivered e.g. to a dental technician in an unassembled state as a kit of components. In some embodiments, the kit of components for the device 1 comprises the attachment member 4, the abutment holder 5, and the connecting member 6.

In the above description, reference has been made to straight abutments, to which the attachment member is attached. A slightly angled abutment may equally substitute the straight abutment, such as an angled abutment angled approximately 17 degrees relative the component to which it is to be attached. The angle may be determined relative interface surfaces for attachment to other components.

The present invention has been described above with reference to specific embodiments. However, other embodiments than the above described are possible within spirit and the scope of the invention. Different method steps than those described above may be provided within the scope of the invention. The different features and steps of the invention may be combined in other combinations than those described. The scope of the invention is only limited by the appended patent claims.

What is claimed is:

1. A method for assembling a device for transferring the rotational position of an angled abutment from a model to an implant installed in the jawbone of a patient, said method comprising:
   installing a first implant replica in a model;
   installing a second implant replica in the model;
   attaching an attachment member to the first implant replica;
   attaching an angled abutment to the second implant replica;
   attaching an abutment holder to the angled abutment;
   connecting a connecting member to the attachment member;
   connecting the connecting member to the abutment holder;
   releasing the attachment member from the first implant replica; and
   releasing the angled abutment from the second implant replica, wherein the rotational position of the angled abutment relative to the second implant replica and a fixed spatial relationship between the attachment member and the abutment holder are maintained after releasing the angled abutment from the second implant replica thereby making a device for transferring the rotational position of an angled abutment from a model to an implant installed in the jawbone of a patient.

2. The method according to claim 1, wherein installing the first implant replica and installing the second implant replica in the model comprises installing with a surgical template.

3. The method according to claim 2, wherein attaching the attachment member to the first implant replica comprises tightening the attachment member to the first implant replica.

4. The method according to claim 2, wherein attaching the angled abutment to the second implant replica comprises tightening the angled abutment to the second implant replica.

5. The method according to claim 2, wherein the connecting member comprises a wire, and the method further comprises attaching the wire of the connecting member to the attachment member and to the angled abutment.

6. The method according to claim 5, wherein attaching the wire comprises using an acrylic resin to attach the wire of the connecting member to the attachment member and to the angled abutment.

7. The method according to claim 5, wherein the wire is dental floss, and the method further comprises attaching the dental floss to the attachment member and to the angled abutment.

8. The method according to claim 2, wherein the connecting member comprises at least one elongated rod having a fastening member, the method comprising coupling the fastening member to the attachment member and to the angled abutment.

9. The method according to claim 8, wherein the fastening member comprises a releaseable coupler, and the method further comprises releasably coupling the connecting member to the attachment member and to the angled abutment.

10. A method for assembling a device for transferring the rotational position of an angled abutment from a model to an implant installed in the jawbone of a patient, said method comprising:
    installing a first implant replica in a model;
    installing a second implant replica in the model;
    coupling an attachment member to the first implant replica;
    coupling an angled abutment to the second implant replica;
    coupling a connect member to the attachment member;
    coupling the connect member to the angled abutment;
    releasing the attachment member from the first implant replica; and
    releasing the angled abutment from the second implant replica, wherein the rotational position of the angled abutment relative to the second implant replica and a fixed spatial relationship between the attachment member and the abutment holder are maintained after releasing the angled abutment from the second implant replica thereby forming a device for transferring the rotational position of an angled abutment from a model to an implant installed in the jawbone of a patient.

11. The method according to claim 10, wherein coupling the connect member to the angled abutment comprises coupling the connect member indirectly to the angled abutment.

12. The method according to claim 11, further comprising coupling an abutment holder to the angled abutment and wherein coupling the connect member to the angled abutment comprises coupling the connect member to the abutment holder.

13. The method according to claim 10, wherein installing the first implant replica and installing the second implant replica in the model comprises installing with a surgical template.

14. The method according to claim 10, wherein attaching the attachment member to the first implant replica comprises tightening the attachment member to the first implant replica.

15. The method according to claim 10, wherein attaching the angled abutment to the second implant replica comprises tightening the angled abutment to the second implant replica.

16. The method according to claim 10, wherein the connect member comprises a wire, and the method further comprises attaching the wire of the connect member to the attachment member and to the angled abutment.

17. The method according to claim 16, wherein attaching the wire comprises using an acrylic resin to attach the wire of the connect member to the attachment member and to the angled abutment.

18. The method according to claim 16, wherein the wire is dental floss, and the method further comprises attaching the dental floss to the attachment member and to the angled abutment.

19. The method according to claim 10, wherein the connect member comprises at least one elongated rod having a fastening member, the method comprising coupling the fastening member to the attachment member and to the angled abutment.

20. The method according to claim 19, wherein the fastening member comprises a releaseable coupler, and the method further comprises releasably coupling the connect member to the attachment member and to the angled abutment.

* * * * *